(12) United States Patent
Fu et al.

(10) Patent No.: US 11,040,996 B2
(45) Date of Patent: *Jun. 22, 2021

(54) METHOD FOR PREPARING NICOTINAMIDE MONONUCLEOTIDE (NMN)

(71) Applicant: BONTAC BIO-ENGINEERING(SHENZHEN) CO., LTD, Shenzhen (CN)

(72) Inventors: Rongzhao Fu, Shenzhen (CN); Qi Zhang, Shenzhen (CN)

(73) Assignee: BONTAC BIO-ENGINEERING(SHENZHEN) CO., LTD, Shenzhen (CN)

( * ) Notice: Subject to any disclaimer, the term of this patent is extended or adjusted under 35 U.S.C. 154(b) by 680 days.

This patent is subject to a terminal disclaimer.

(21) Appl. No.: 15/574,851

(22) PCT Filed: Jul. 30, 2016

(86) PCT No.: PCT/CN2016/092458
§ 371 (c)(1),
(2) Date: Nov. 17, 2017

(87) PCT Pub. No.: WO2017/185549
PCT Pub. Date: Nov. 2, 2017

(65) Prior Publication Data
US 2018/0162895 A1    Jun. 14, 2018

(51) Int. Cl.
| C07H 19/048 | (2006.01) |
| C07H 19/207 | (2006.01) |
| C12N 9/10 | (2006.01) |
| C07H 1/04 | (2006.01) |
| C12P 19/30 | (2006.01) |

(52) U.S. Cl.
CPC .......... C07H 19/048 (2013.01); C07H 1/04 (2013.01); C07H 19/207 (2013.01); C12N 9/1077 (2013.01); C12P 19/30 (2013.01); C12Y 207/01015 (2013.01); C12Y 207/06001 (2013.01); C12Y 204/02012 (2013.01)

(58) Field of Classification Search
CPC .... C12Y 204/02012; C12Y 207/01015; C12Y 207/06001; C07H 19/048; C07H 19/207; C12N 9/1077
See application file for complete search history.

(56) References Cited

U.S. PATENT DOCUMENTS

2009/0246803 A1 * 10/2009 Imai ........................ C12P 19/36
435/7.8

FOREIGN PATENT DOCUMENTS

| CN | 101601679 A | 12/2009 |
| CN | 104367587 A | 2/2015 |
| CN | 104814974 A | 8/2015 |
| CN | 104817604 A | 8/2015 |
| WO | 2015069860 A1 | 5/2015 |
| WO | 2015148522 A1 | 10/2015 |

OTHER PUBLICATIONS

Gross et al., J. Am. Chem. Soc. 1983, 105:7428-7435 (Year: 1983).*
Kim et al., JMB, 2006, 362:66-77 (Year: 2006).*
Feifeng Sheng et al, Effect of nicotinamide mononucleotide on insulin secretion and gene expressions of PDX-1 and FoxO1 in RIN-m5f cells, J Cent South Univ (Med Sci), Dec. 31, 2011, Issue No. 10, vol. 36, ISSN: 1672-7347, p. 958-963.
Jun Yoshino et al, Nicotinamide mononucleotide, a key NAD+ intermediate, treats Cell Metabolism, Oct. 5, 14(4) 528-536

* cited by examiner

*Primary Examiner* — Allison M Fox
*Assistant Examiner* — Qing Xu
(74) *Attorney, Agent, or Firm* — Bayramoglu Law Offices LLC

(57) ABSTRACT

The present invention provides a method for preparing nicotinamide mononucleotide (NMN) by bioanalysis. The method includes a step of catalytically reacting a plurality of raw materials including nicotinamide, ATP, and ribose in the presence of nicotinamide phosphoribosyltransferase (Nampt), ribose phosphate pyrophosphokinase, and ribokinase, to prepare the NMN.

7 Claims, No Drawings
Specification includes a Sequence Listing.

ND FOR PREPARING
METHOD FOR PREPARING NICOTINAMIDE MONONUCLEOTIDE (NMN)

CROSS REFERENCE TO RELATED APPLICATIONS

This application is the national phase entry of International Application No. PCT/CN2016/092458, filed on Jul. 30, 2016, the entire contents of which are incorporated herein by reference.

TECHNICAL FIELD

The present invention relates to the technical field of molecular biology and biotechnology, and particularly to a method for preparing nicotinamide mononucleotide (NMN) by biocatalysis.

SEQUENCE LISTING

The instant application contains a Sequence Listing which has been submitted in ASCII format via EFS-Web and is hereby incorporated by reference in its entirety. Said ASCII copy is named "GBQN010_sequence_listing.txt" and is 15,568 bytes in size.

BACKGROUND OF THE INVENTION

Nicotinamide mononucleotide (NMN) is a biochemical substance present in biological cells, which is adenylated by nicotinamide mononucleotide adenylyltransferase to convert into an important substance nicotinamide adenine dinucleotide (NAD, also referred to as coenzyme I) essential to the survival of biological cells. NMN directly participates in the transfer of adenosine in vivo, and the intracellular level of which has a direct influence on the NAD content. NMN plays an important role in the energy production in biological cells, and is harmless to human body.

Up to now, it has been found that NMN has many medical and healthcare uses in, for example, slowing down the aging process, treating Parkinson's disease and other senile diseases, regulating the insulin secretion, and affecting the mRNA expression, and many other uses are still under development. The demand for NMN in the market is increased constantly as a result of increased insight into the medicinal and healthcare effects of NMN and the wide use of NMN as a reactive substrate in the chemical industry.

At present, the method for preparing NMN mainly include: 1. yeast fermentation; 2. chemical synthesis; and 3. biocatalysis. Chemical synthesis has the disadvantages of high cost and production of chiral compounds. The NMN produced by yeast fermentation contains some organic solvent residue. Biocatalysis is the most environmentally-friendly pollution-free method for preparing NMN, because no organic solvent residue and no problem of chirality are present and the prepared NMN is an isoform of that existing in an organism. In the existing biocatalytic method for preparing NMN, nicotinamide and 5'-phosphoribosyl-1'-pyrophosphate (PRPP) are generally used as substrates for preparing NMN in the presence of nicotinamide phosphoribosyltransferase (Nampt) as a catalyst. However, due to the high price and limited sources of PRPP, the biocatalytic method suffers from high production cost, which seriously restricts its application and development.

Therefore, there is a need for developing a new method for preparing NMN by biocatalysis without using PRPP as a substrate.

SUMMARY OF THE INVENTION

In view of the problems existing in the methods for preparing nicotinamide mononucleotide (NMN) in the prior art, an object of the present invention is to provide a new method for preparing NMN by biocatalysis, in which the use of PRPP of high price and limited sources as a substrate is avoided, and which has the advantages of low cost, being environmentally-friendly and pollution-free, and being applicable to large-scale industrial production.

To achieve the above object, a method for preparing NMN is finally developed by the present inventors after long-term extensive experimental explorations. The method comprises: catalytically reacting nicotinamide, ATP, and ribose as raw materials, in the presence of Nampt, ribose phosphate pyrophosphokinase, and ribokinase, to prepare NMN.

According to the international system of nomenclature for enzymes, the EC numbers of the enzymes used in the method are respectively Nampt EC 2.4.2.12, ribose phosphate pyrophosphokinase EC 2.7.6.1, and ribokinase EC 2.7.1.15.

The enzymes used in the methods may exist in various particular forms, including enzyme solutions, enzyme lyophilized powders, enzyme-containing cells, and various immobilized enzymes and immobilized enzyme-containing cells, and may exist as non-purified crude enzymes, or are partially or fully purified.

In order to improve the stability and the reuse rate of the enzymes used, so as to better accomplish the above-mentioned catalytic reaction and to further reduce the cost, it is preferable to use immobilized enzymes in the above method. The immobilized enzyme is substantially prepared as follows. The enzyme is diluted to a protein content of 5-10 mg/ml with an enzyme washing buffer (0.02 M Tris-HCl/0.001 M EDTA solution, pH 7.0), equal volumes of the enzyme dilution and a PB solution (2.0 mol/L potassium dihydrogen phosphate, pH 7.5) are mixed, and then an enzyme immobilizing carrier (50 mg of enzyme/g of carrier) is added and reacted at 25° C. for 20 hrs in a shaker (at a rotation speed of 150 rpm). After the reaction is completed, the system is filtered with a filter bag and washed 5-6 times with the enzyme washing buffer, to obtain the immobilized enzyme. The enzyme immobilizing carrier may be, for example, epoxy-type LX-3000, silica, activated carbon, glass beads, and macroporous polyN-aminoethyl acrylamide-polyethylene.

Preferably, the reaction takes place at a temperature of 30-50° C. and a pH of 6.5-8.5.

More preferably, the reaction takes place at a temperature of 35-45° C. and a pH of 7.0-8.0, upon which the conversion rate is the maximum.

Preferably, the reaction takes place in the presence of $Mg^{2+}$ and $K^+$.

Preferably, the reaction takes place in a Tris-HCl buffer.

Preferably, the concentration of the nicotinamide is 1-150 mM, the concentration of the ATP is 1-50 mM, and the concentration of the ribose is 1-100 mM.

Preferably, the molar ratio of the raw materials nicotinamide, ATP, and ribose is 1-4:1:1-4. When the raw materials are fed at such a ratio, the ATP can be reacted fully with a conversion rate of 80-100%. Among the three raw materials, ATP is the most expensive, so the production cost can be largely reduced by this ratio. More preferably, the molar ratio of the raw materials nicotinamide, ATP, and ribose is 1.5:1:1.5, upon which the reaction conversion rate based on the substrate ATP is 100%, and the cost is the minimum.

The crude NMN product solution obtained after the reaction can be filtered, purified, and dried through conventional technical means known in the art, to obtain the product NMN.

Preferably, the Nampt used in the method is a protein of (a) or (b) shown below:

(a) a protein having an amino acid sequence as shown in SEQ ID NO: 3; and (b) a protein derived from (a) by substitution, deletion, or insertion of one or more amino acids in the amino acid sequence as defined in (a), and having Nampt catalytic activity for the substrates nicotinamide and PRPP that is higher than a parent having an amino acid sequence as shown in SEQ ID NO: 2.

The Nampt includes a series of Nampt mutants having high catalytic activity, obtained by the present inventors by site-directed mutation of parent Nampt gene derived from *Meiothermus ruber* DSM 1279 and having a nucleotide sequence as shown in SEQ ID NO: 1, PCR amplification, insertion into a suitable vector, and then screening in a LB+ Kanamycin medium. By means of the high catalytic activity of these mutants, the cost for producing NMN by biocatalysis in the industry can be greatly reduced, so these mutants have a high application value in the industry.

Preferably, the Nampt has at least one mutation at at least one position selected from positions 180, 182, 231, 298, 338, and 377, compared with the amino acid sequence as shown in SEQ ID NO: 2.

More preferably, the Nampt has at least one of the mutations F180A, F180W, A182Y, E231A, E231Q, D298A, D298N, D298E, D338N, D338E, D377A, D377N, and D377E.

BENEFICIAL EFFECT

1. Compared with the existing methods for preparing NMN, in the method provided in the present invention, the disadvantages of chemical synthesis and yeast fermentation are overcome, the use of PRPP of high cost and limited sources is successfully avoided, and the conversion rate based on the substrate ATP is up to 100%. Therefore, the present method is the most environmentally-friendly pollution-free method for preparing NMN, and is applicable to large-scale industrial production with low cost.

2. The Nampt used in the method provided in the present invention is a mutant obtained through artificially induced site-directed mutation. Compared with the existing wild Nampt, the enzymatic activity of the mutant is considerably increased. As shown in an enzyme activity assay with nicotinamide and PRPP as substrates, the enzymatic activity of the mutant is 1.2-6.9 times of the enzymatic activity of the parent. Such a high catalytic activity allows the mutant to be used in the form of a crude enzyme without purification, or be used merely after partial purification. This results in a greatly reduced cost in the catalytic production of NMN by using the Nampt mutant provided in the present invention, thus bringing about high market competitiveness, and enabling the method for producing NMN by biocatalysis to be applicable to large-scale industrial production.

DETAILED DESCRIPTION OF THE INVENTION

The present invention will be described in further detail with reference to specific examples. The following examples are illustrative of the present invention and the present invention is not limited thereto. Where no specific conditions are given in the examples, conventional conditions or conditions recommended by a manufacturer are adopted.

In the method for preparing NMN provided in the present invention, a one-step feed mode in which all the raw materials and the enzymes are added at a time or a stepwise feed mode may be used. The one-step feed mode has the advantages of simple operation and short reaction time, and the stepwise feed mode has the advantages of complete reaction and high conversion rate. The specific implementation processes are as follows.

One-Step Feed Mode:

The raw materials are dissolved in water, to formulate a substrate solution having a composition comprising 1-150 mM nicotinamide, 1-50 mM ATP, 1-100 mM ribose, 1-30 mM $MgCl_2$, 1-20 mM KCl, and 50-100 mM Tris-HCl buffer, which is then adjusted pH 6.5-8.5. Then, various catalytic enzymes were added to the substrate solution in amounts of 1-100 g of Nampt/L of substrate solution, 1-100 g of ribose phosphate pyrophosphokinase/L of substrate solution, and 1-100 g of ribokinase/L of substrate solution. The system is stirred until uniform and then reacted. During the reaction process, stirring is continued (at a stirring speed of 50 rpm), the reaction temperature is controlled at 30-50° C., and the pH is maintained at 6.5-8.5. After 1-8 hrs of reaction, a crude NMN product solution is obtained, which is filtered, purified, and dried, to obtain a product NMN.

Stepwise Feed Mode:

The raw materials are dissolved in water, to formulate a substrate solution having a composition comprising 1-50 mMATP, 1-100 mM ribose, 1-30 mM $MgCl_2$, 1-20 mM KCl, and 50-100 mM Tris-HCl buffer, which is then adjusted to pH 6.5-8.5. Then, the catalytic enzymes: 1-100 g of ribose phosphate pyrophosphokinase/L of substrate solution, and 1-100 g of ribokinase/L of substrate solution are added to the substrate solution. The system is stirred until uniform and then reacted. During the reaction process, stirring is continued (at a stirring speed of 50 rpm), the reaction temperature is controlled at 30-50° C., and the pH is maintained at 6.5-8.5.

After 1-8 hrs of reaction, the reaction solution is separated, and then 1-100 mM nicotinamide, 1-30 mM $MgCl_2$, 50-100 mM Tris-HCl buffer and 1-100 g of Nampt/L of substrate solution are added to the reaction solution, stirred until uniform, and continuously reacted. During the reaction process, stirring is continued (at a stirring speed of 50 rpm), the reaction temperature is controlled at 30-50° C., and the pH is maintained at 6.5-8.5. After additional 1-8 hrs of reaction, a crude NMN product solution is obtained, which is filtered, purified, and dried, to obtain a product NMN.

For the enzymes used in the following examples, except that the Nampt mutant is obtained through artificially induced site-directed mutation of parent Nampt gene derived from *Meiothermus ruber* DSM 1279 and having a nucleotide sequence as shown in SEQ ID NO: 1, the remaining Nampt, ribose phosphate pyrophosphokinase, and ribokinase are all enzyme lyophilized powders directly purchased from the market.

Example 1

Preparation of NMN

A substrate solution containing 1 mM nicotinamide, 1 mM ATP, 1 mM ribose, 1 mM $MgCl_2$, 1 mM KCl, and 50 mM Tris-HCl buffer was added to a reactor and adjusted to pH 6.5-7.0. Then, various catalytic enzymes were added to the substrate solution in amounts of 1 g of Nampt/L of substrate solution, 1 g of ribose phosphate pyrophosphokinase/L of substrate solution, and 1 g of ribokinase/L of substrate solution. The system was stirred until uniform and then reacted. During the reaction process, stirring was continued (at a stirring speed of 50 rpm), the reaction temperature was controlled at 30° C., and the pH was maintained at 6.5-7.0. After 1 hr of reaction, a crude NMN product solution (containing 0.5 mM NMN) was obtained, which was filtered, purified, and dried, to obtain a product NMN.

Example 2

Preparation of NMN

A substrate solution containing 15 mM ATP, 100 mM ribose, 10 mM $MgCl_2$, 10 mM KCl, and 70 mM Tris-HCl buffer was added to a reactor and adjusted to pH 7.0-7.5. Then, the catalytic enzymes: 20 g of ribose phosphate pyrophosphokinase/L of substrate solution, and 20 g of ribokinase/L of substrate solution were added to the substrate solution. The system was stirred until uniform and then reacted. During the reaction process, stirring was continued (at a stirring speed of 50 rpm), the reaction temperature was controlled at 35° C., and the pH was maintained at 7.0-7.5.

After 3 hrs of reaction, the reaction solution was separated, and fed to another reactor. Then, 60 mM nicotinamide, 10 mM $MgCl_2$, 70 mM Tris-HCl buffer and 20 g of Nampt/L of substrate solution were added to the reaction solution, stirred until uniform, and continuously reacted. During the reaction process, stirring was continued (at a stirring speed of 50 rpm), the reaction temperature was controlled at 35° C., and the pH was maintained at 7.5-8.0. After additional 3 hrs of reaction, a crude NMN product solution (containing 7.3 mM NMN) was obtained, which was filtered, purified, and dried, to obtain a product NMN.

Example 3

Preparation of NMN

A substrate solution containing 35 mM ATP, 70 mM ribose, 20 mM $MgCl_2$, 15 mM KCl, and 100 mM Tris-HCl buffer was added to a reactor and adjusted to pH 7.5-8.0. Then, the catalytic enzymes: 50 g of ribose phosphate pyrophosphokinase/L of substrate solution, and 50 g of ribokinase/L of substrate solution were added to the substrate solution. The system was stirred until uniform and then reacted. During the reaction process, stirring was continued (at a stirring speed of 50 rpm), the reaction temperature was controlled at 40° C., and the pH was maintained at 7.5-8.0.

After 5 hrs of reaction, the reaction solution was separated, and fed to another reactor. Then, 60 mM nicotinamide, 20 mM $MgCl_2$, 100 mM Tris-HCl buffer and 50 g of Nampt/L of substrate solution were added to the reaction solution, stirred until uniform, and continuously reacted. During the reaction process, stirring was continued (at a stirring speed of 50 rpm), the reaction temperature was controlled at 40° C., and the pH was maintained at 7.5-8.0. After additional 5 hrs of reaction, a crude NMN product solution (containing 17.2 mM NMN) was obtained, which was filtered, purified, and dried, to obtain a product NMN.

Example 4

Preparation of NMN

A substrate solution containing 150 mM nicotinamide, 50 mM ATP, 100 mM ribose, 30 mM $MgCl_2$, 20 mM KCl, and 100 mM Tris-HCl buffer was added to a reactor, and adjusted to pH 8.0-8.5. Then, various catalytic enzymes were added to the substrate solution in amounts of 100 g of Nampt/L of substrate solution, 100 g of ribose phosphate pyrophosphokinase/L of substrate solution, and 100 g of ribokinase/L of substrate solution. The system was stirred until uniform and then reacted. During the reaction process, stirring was continued (at a stirring speed of 50 rpm), the reaction temperature was controlled at 50° C., and the pH was maintained at 8.0-8.5. After 8 hrs of reaction, a crude NMN product solution (containing 24.9 mM NMN) was obtained, which was filtered, purified, and dried, to obtain a product NMN.

Example 5

Preparation of NMN

Preparation of immobilized enzyme: Nampt, ribose phosphate pyrophosphokinase, and ribokinase were diluted to a protein content of 5-10 mg/ml with an enzyme washing buffer (0.02 M Tris-HCl/0.001 M EDTA solution, pH 7.0) respectively, equal volumes of the enzyme dilution and a PB solution (2.0 mol/L potassium dihydrogen phosphate, pH 7.5) were mixed, and then an enzyme immobilizing carrier epoxy-type LX-3000 (50 mg of enzyme/g of carrier) was added and reacted at 25° C. for 20 hrs in a shaker (at a rotation speed of 150 rpm). After the reaction was completed, the system was filtered with a filter bag and washed 5-6 times with the enzyme washing buffer, to obtain immobilized Nampt, immobilized ribose phosphate pyrophosphokinase, and immobilized ribokinase respectively.

A substrate solution containing 30 mM nicotinamide, 20 mM ATP, 30 mM ribose, 15 mM $MgCl_2$, 15 mM KCl, and 100 mM Tris-HCl buffer was added to a reactor, and adjusted to pH 7.0-7.5. Then, various catalytic enzymes were added to the substrate solution in amounts of 10 g of immobilized Nampt/L of substrate solution, 10 g of immobilized ribose phosphate pyrophosphokinase/L of substrate solution, and 10 g of immobilized ribokinase/L of substrate solution. The system was stirred until uniform and then reacted. During the reaction process, stirring was continued (at a stirring speed of 50 rpm), the reaction temperature was controlled at 37° C., and the pH was maintained at 7.0-7.5. After 4 hrs of reaction, a crude NMN product solution (containing 10 mM NMN) was obtained, which was filtered, purified, and dried, to obtain a product NMN.

Example 6

Preparation of Nampt mutants

A process for preparing Nampt mutants used in the method provided in the present invention through artificially induced site-directed mutation was substantially as follows. A plasmid vector containing parent Nampt gene was constructed. Then a site for site-directed mutation and the type of the amino acid after mutation were determined. Suitable primers were synthesized, DNA fragments were amplified by PCR using the plasmid vector containing parent Nampt gene as a template, the amplified DNA fragments were assembled, and the full-length mutant gene was amplified by PCR. Then, the full-length mutant gene was cloned onto a suitable vector, then transformed into suitable host cells, and incubated, to screen out positive clones having Nampt activity. Plasmid DNA was extracted from the positive clones, and sequenced, to determine the mutation introduced. After a fragment of interest is determined to be inserted into the vector, the clones were screened in a LB+ Kanamycin medium, to obtain a series of Nampt mutants having high catalytic activity.

In the preparation method, any suitable vectors may be used, for example, prokaryotic expression vectors such as pRSET, pES21, and the like; and cloning vectors such as pUC18/19 and pBluscript-SK. In the present invention, pRSET-A is preferably used as a vector. The host cell to which the vector is transferred may be a prokaryotic cell including *Escherichia coli* or an eukaryotic cell including *Saccharomyces cerevisiae* and *Pichia pastoris*.

I. Construction of Plasmid Vector Containing Parent Nampt Gene

Whole sequence artificial synthesis was performed on the parent Nampt gene sequence publicized in the Genebank (GenBank Accession No.: CP001743.1) derived from *Meiothermus ruber* DSM 1279 (by a commercial synthesis company). The synthesized product was enzymatically cleaved by the restriction endonucleases NdeI and BamHI, and then ligated to the vector pRSET-A (available from Invitrogen, USA) that was also enzymatically cleaved by the restriction endonucleases NdeI and BamHI, to obtain plasmid pRSET-nampt. After DNA sequencing, it is determined that the nucleotide sequence of the cloned parent Nampt gene is as shown in SEQ ID NO: 1, and the amino acid sequence is as shown in SEQ ID NO: 2.

II. Preparation of Nampt Mutant

PCR amplification reaction system: 20 mM Tris-HCl (pH 8.8), 10 mM KCl, 10 mM $(NH_4)_2SO_4$, 2 mM $MgSO_4$, 0.1% Triton X-100, 50 mM dATP, 50 mM dTTP, 50 mM dCTP, 50 mM dGTP, 1.5 U Pfu DNA polymerase (Promega, USA), 20 ng DNA template, and 400 nM upstream primer, and 400 nM downstream primer, where the reaction volume was adjusted to 50 μl with sterile water.

PCR amplification reaction conditions: 3 min at 95° C.; 35 cycles of: 50 s at 95° C., 30 s at 52° C., and 3 min at 72° C.; and finally 5 min at 72° C.

1. Preparation of F180A Mutant

The primer pair F180A-F: 5' GTT-CAAACTGCACGACGCGGGTGCTCGTGGTGTTTC 3' (SEQ ID NO: 4) and F180A-R: 5' GAAACAC-CACGAGCACCCGCGTCGTGCAGTTTGAAC 3' (SEQ ID NO: 5) were used. The plasmid pRSET-nampt constructed in Section I of Example 6 was used as a template. The F180A mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-F180A. The plasmid pRSET-F180A was transformed into competent bacterial cells *E. coli* BL21, and clones having Nampt activity were screened out on a Luria broth (LB) plate (containing 50 mg/L Kanamycin). Plasmid pRSET-F180A DNA was extracted from the clones, and sequenced to determine that the point mutation introduced was correct. Compared with the parent amino acid sequence as shown in SEQ ID NO: 2, the amino acid sequence of the F180A mutant is as shown in SEQ ID NO: 3 and has a mutation of Phe (F) to Ala (A) at position 180.

2. Preparation of F180W Mutant

The primer pair F180W-F: 5' GTT-CAAACTGCACGACTGGGGTGCTCGTGGTGTTTC 3' (SEQ ID NO: 6) and F180W-R: 5' GAAACAC-CACGAGCACCCCAGTCGTGCAGTTTGAAC 3' (SEQ ID NO: 7) were used. The plasmid pRSET-nampt constructed in Section I of Example 6 was used as a template. The F180W mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-F180W The plasmid pRSET-F180W was transformed into competent bacterial cells *E. coli* BL21, and clones having Nampt activity were screened out on a Luria broth (LB) plate (containing 50 mg/L Kanamycin). Plasmid pRSET-F180W DNA was extracted from the clones, and sequenced to determine that the point mutation introduced was correct. Compared with the parent amino acid sequence as shown in SEQ ID NO: 2, the amino acid sequence of the F180W mutant has a mutation of Phe (F) to Trp (W) at position 180.

3. Preparation of A182Y Mutant

The primer pair A182Y-F: 5' CAAACTGCACGACTTCGGT-TATCGTGGTGTTTCTTCTCTG 3' (SEQ ID NO: 8) and A182Y-R:5'CAGAGAAGAAACACCACGA-TAACCGAAGTCGTGCAGTTTG3'(SEQ ID NO: 9) were used. The plasmid pRSET-nampt constructed in Section I of Example 6 was used as a template. The A182Y mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-A182Y The plasmid pRSET-A182Y was transformed into competent bacterial cells *E. coli* BL21, and clones having Nampt activity were screened out on a Luria broth (LB) plate (containing 50 mg/L Kanamycin). Plasmid pRSET-A182Y DNA was extracted from the clones, and sequenced to determine that the point mutation introduced was correct. Compared with the parent amino acid sequence as shown in SEQ ID NO: 2, the amino acid sequence of A182Y mutant has a mutation of Ala (A) to Tyr (Y) at position 182.

4. Preparation of E231A Mutant

The primer pair E231A-F: 5' CTATCCCGGC-TATGGCGCACTCTACCGTTAC 3' (SEQ ID NO: 10) and E231A-R: 5' GTAACGGTAGAGTGCGCCATAGCCGG-GATAG 3' (SEQ ID NO: 11) were used. The plasmid pRSET-nampt constructed in Section I of Example 6 was used as a template. The E231A mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-E231A. The plasmid pRSET-E231A was transformed into competent bacterial cells *E. coli* BL21, and clones having Nampt activity were screened out on a Luria broth (LB) plate (containing 50 mg/L Kanamycin). Plasmid pRSET-E231A DNA was extracted from the clones, and sequenced to determine that the point mutation introduced was correct. Compared with the parent amino acid sequence as shown in SEQ ID NO: 2, the amino acid sequence of the E231A mutant has a mutation of Glu (E) to Ala (A) at position 231.

5. Preparation of E231Q Mutant

The primer pair E231Q-F: 5' CTCTATCCCGGC-TATGCAGCACTCTACCGTTACC 3' (SEQ ID NO: 12) and E231Q-R: 5' GGTAACGGTAGAGTGCTGCAT-AGCCGGGATAGAG 3' (SEQ ID NO: 13) were used. The plasmid pRSET-nampt constructed in Section I of Example 6 was used as a template. The E231Q mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-E231Q. The plasmid pRSET-E231Q was transformed into competent bacterial cells E. coli BL21, and clones having Nampt activity were screened out on a Luria broth (LB) plate (containing 50 mg/L Kanamycin). Plasmid pRSET-E231Q DNA was extracted from the clones, and sequenced to determine that the point mutation introduced was correct. Compared with the parent amino acid sequence as shown in SEQ ID NO: 2, the amino acid sequence of E231Q mutant has a mutation of Glu (E) to Gln (Q) at position 231.

6. Preparation of D298A Mutant

The primer pair D298A-F: 5' TATCCGTCCGGCGTCTGGTGACCC 3' (SEQ ID NO: 14) and D298A-R: 5' GGGTCACCAGACGCCGGACGGATA 3' (SEQ ID NO: 15) were used. The plasmid pRSET-nampt constructed in Section I of Example 6 was used as a template. The D298A mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-D298A. The plasmid pRSET-D298A was transformed into competent bacterial cells E. coli BL21, and clones having Nampt activity were screened out on a Luria broth (LB) plate (containing 50 mg/L Kanamycin). Plasmid pRSET-D298A DNA was extracted from the clones, and sequenced to determine that the point mutation introduced was correct. Compared with the parent amino acid sequence as shown in SEQ ID NO: 2, the amino acid sequence of the D298A mutant has a mutation of Asp (D) to Ala (A) at position 298.

7. Preparation of D298N Mutant

The primer pair D298N-F: 5' GTTGT-TATCCGTCCGAATTCTGGTGACCCGCCG 3' (SEQ ID NO: 16) and D298N-R: 5' CGGCGGGTCACCAGAAT-TCGGACGGATAACAAC 3' (SEQ ID NO: 17) were used. The plasmid pRSET-nampt constructed in Section I of Example 6 was used as a template. The D298N mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-D298N. The plasmid pRSET-D298N was transformed into competent bacterial cells E. coli BL21, and clones having Nampt activity were screened out on a Luria broth (LB) plate (containing 50 mg/L Kanamycin). Plasmid pRSET-D298N DNA was extracted from the clones, and sequenced to determine that the point mutation introduced was correct. Compared with the parent amino acid sequence as shown in SEQ ID NO: 2, the amino acid sequence of the D298N mutant has a mutation of Asp (D) to Asn (N) at position 298.

8. Preparation of D298E Mutant

The primer pair D298E-F: 5' GTTGTTATCCGTCCG-GAATCTGGTGACCCGCCGTTC 3' (SEQ ID NO: 18) and D298E-R: 5' GAACGGCGGGTCACCAGAT-TCCGGACGGATAACAAC 3' (SEQ ID NO: 19) were used. The plasmid pRSET-nampt constructed in Section I of Example 6 was used as a template. The D298E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-D298E. The plasmid pRSET-D298E was transformed into competent bacterial cells E. coli BL21, and clones having Nampt activity were screened out on a Luria broth (LB) plate (containing 50 mg/L Kanamycin). Plasmid pRSET-D298E DNA was extracted from the clones, and sequenced to determine that the point mutation introduced was correct. Compared with the parent amino acid sequence as shown in SEQ ID NO: 2, the amino acid sequence of the D298E mutant has a mutation of Asp (D) to Glu (E) at position 298.

9. Preparation of D338N Mutant

The primer pair D338N-F: 5' GTTCGTGT-TATCCAGGGTAATGGTGTTAACGCTGACTC 3' (SEQ ID NO: 20) and D338N-R: 5' GAGTCAGCGTTAACAC-CATTACCCTGGATAACACGAAC 3' (SEQ ID NO: 21) were used. The plasmid pRSET-nampt constructed in Section I of Example 6 was used as a template. D338N mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-D338N. The plasmid pRSET-D338N was transformed into competent bacterial cells E. coli BL21, and clones having Nampt activity were screened out on a Luria broth (LB) plate (containing 50 mg/L Kanamycin). Plasmid pRSET-D338N DNA was extracted from the clones, and sequenced to determine that the point mutation introduced was correct. Compared with the parent amino acid sequence as shown in SEQ ID NO: 2, the amino acid sequence of the D338N mutant has a mutation of Asp (D) to Asn (N) at position 338.

10. Preparation of D338E Mutant

The primer pair D338E-F: 5' GTTATCCAGGGT-GAAGGTGTTAACGCTGAC 3' (SEQ ID NO: 22) and D338E-R: 5' GTCAGCGTTAACACCTTCACCCTGGA-TAAC 3' (SEQ ID NO: 23) were used. The plasmid pRSET-nampt constructed in Section I of Example 6 was used as a template. The D338E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-D338E. The plasmid pRSET-D338E was transformed into competent bacterial cells E. coli BL21, and clones having Nampt activity were screened out on a Luria broth (LB) plate (containing 50 mg/L Kanamycin). Plasmid pRSET-D338E DNA was extracted from the clones, and sequenced to determine that the point mutation introduced was correct. Compared with the parent amino acid sequence as shown in SEQ ID NO: 2, the amino acid sequence of the D338E mutant has a mutation of Asp (D) to Glu (E) at position 338.

11. Preparation of D377A Mutant

The primer pair D377A-F: 5' CACCCGCACCGTGCGACCCAGAAATTC 3' (SEQ ID NO: 24) and D377A-R: 5' GAATTTCTGGGTCGCACGGTGCGGGTG 3' (SEQ ID NO: 25) were used. The plasmid pRSET-nampt constructed in Section I of Example 6 was used as a template. The D377A mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-D377A. The plasmid pRSET-D377A was transformed into competent bacterial cells E. coli BL21, and clones having Nampt activity were screened out on a Luria broth (LB) plate (containing 50 mg/L Kanamycin). Plasmid pRSET-D377A DNA was extracted from the clones, and sequenced to determine that the point mutation introduced was correct. Compared with the parent amino acid sequence as shown in SEQ ID NO: 2, the amino acid sequence of the D377A mutant has a mutation of Asp (D) to Ala (A) at position 377.

12. Preparation of D377N Mutant

The primer pair D377N-F: 5' GCAACACCCGCACCGTAATACCCAGAAATTCGCTC 3' (SEQ ID NO: 26) and D377N-R: 5' GAGCGAATTTCTGGGTATTACGGTGCGGGTGTTGC 3' (SEQ ID NO: 27) were used. The plasmid pRSET-nampt constructed in Section I of Example 6 was used as a template. The D377N mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-D377N. The plasmid pRSET-D377N was transformed into competent bacterial cells E. coli BL21, and clones having Nampt activity were screened out on a Luria broth (LB) plate (containing 50 mg/L Kanamycin). Plasmid pRSET-D377N DNA was extracted from the clones, and sequenced to determine that the point mutation introduced was correct. Compared with the parent amino acid sequence as shown in SEQ ID NO: 2, the amino acid sequence of the D377N mutant has a mutation of Asp (D) to Asn (N) at position 377.

13. Preparation of D377E Mutant

The primer pair D377E-F: 5' CCCGCACCGTGAAACCCAGAAATTCG 3' (SEQ ID NO: 28) and D377E-R: 5' CGAATTTCTGGGTTTCACGGTGCGGG 3' (SEQ ID NO: 29) were used. The plasmid pRSET-nampt constructed in Section I of Example 6 was used as a template. The D377E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-D377E. The plasmid pRSET-D377E was transformed into competent bacterial cells E. coli BL21, and clones having Nampt activity were screened out on a Luria broth (LB) plate (containing 50 mg/L Kanamycin). Plasmid pRSET-D377E DNA was extracted from the clones, and sequenced to determine that the point mutation introduced was correct. Compared with the parent amino acid sequence as shown in SEQ ID NO: 2, the amino acid sequence of the D377E mutant has a mutation of Asp (D) to Glu (E) at position 377.

14. Preparation of E231Q/D338E Mutant

The primer pair D338E-F: 5' GTTATCCAGGGTGAAGGTGTTAACGCTGAC 3' (SEQ ID NO: 22) and D338E-R: 5' GTCAGCGTTAACACCTTCACCCTGGATAAC 3' (SEQ ID NO: 23) were used. The plasmid pRSET-E231Q constructed in Subsection 5 in Section II of Example 6 was used as a template. The E231Q/D338E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-21. The plasmid pRSET-21 was transformed into competent bacterial cells E. coli BL21, and clones having Nampt activity were screened out on a Luria broth (LB) plate (containing 50 mg/L Kanamycin). Plasmid pRSET-21 DNA was extracted from the clones, and sequenced to determine that the point mutation introduced was correct. Compared with the parent amino acid sequence as shown in SEQ ID NO: 2, the amino acid sequence of the E231Q/D338E mutant has a mutation of Glu (E) to Gln (Q) at position 231, and a mutation of Asp (D) to Glu (E) at position 338.

15. Preparation of E231Q/D377E Mutant

The primer pair D377E-F: 5' CCCGCACCGTGAAACCCAGAAATTCG 3' (SEQ ID NO: 28) and D377E-R: 5' CGAATTTCTGGGTTTCACGGTGCGGG 3' (SEQ ID NO: 29) were used. The plasmid pRSET-E231Q constructed in Subsection 6 in Section II of Example 6 was used as a template. The E231Q/D377E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-22. The plasmid pRSET-22 was transformed into competent bacterial cells E. coli BL21, and clones having Nampt activity were screened out on a Luria broth (LB) plate (containing 50 mg/L Kanamycin). Plasmid pRSET-22 DNA was extracted from the clone, and sequenced to determine that the point mutation introduced was correct. Compared with the parent amino acid sequence as shown in SEQ ID NO: 2, the amino acid sequence of the E231Q/D377E mutant has a mutation of Glu (E) to Gln (Q) at position 231 and a mutation of Asp (D) to Glu (E) at position 377.

16. Preparation of D338E/D377E Mutant

The primer pair D377E-F: 5' CCCGCACCGTGAAACCCAGAAATTCG 3' (SEQ ID NO: 28) and D377E-R: 5' CGAATTTCTGGGTTTCACGGTGCGGG 3' (SEQ ID NO: 29) were used. The plasmid pRSET-D338E constructed in Subsection 10 in Section II of Example 6 was used as a template. The D338E/D377E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-23. The plasmid pRSET-23 was transformed into competent bacterial cells E. coli BL21, and clones having Nampt activity were screened out on a Luria broth (LB) plate (containing 50 mg/L Kanamycin). Plasmid pRSET-23 DNA was extracted from the clone, and sequenced to determine that the point mutation introduced was correct. Compared with the parent amino acid sequence as shown in SEQ ID NO: 2, the amino acid sequence of the D338E/D377E mutant has a mutation of Asp (D) to Glu (E) at position 338 and a mutation of Asp (D) to Glu (E) at position 377.

17. Preparation of E231Q/D338E/D377E Mutant

The primer pair D377E-F: 5' CCCGCACCGT-GAAACCCAGAAATTCG 3' (SEQ ID NO: 28) and D377E-R: 5' CGAATTTCTGGGTTTCACGGTGCGGG 3' (SEQ ID NO: 29) were used. The plasmid pRSET-21 constructed in Subsection 14 in Section II of Example 6 was used as a template. The E231Q/D338E/D377E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-31. The plasmid pRSET-31 was transformed into competent bacterial cells E. coli BL21, and clones having Nampt activity were screened out on a Luria broth (LB) plate (containing 50 mg/L Kanamycin). Plasmid pRSET-31 DNA was extracted from the clone, and sequenced to determine that the point mutation introduced was correct. Compared with the parent amino acid sequence as shown in SEQ ID NO: 2, the amino acid sequence of the E231Q/D338E/D377E mutant has a mutation of Glu (E) to Gln (Q) at position 231, a mutation of Asp (D) to Glu (E) at position 338, and a mutation of Asp (D) to Glu (E) at position 377.

18. Preparation of E231Q/D298A/D338E/D377E Mutant

The primer pair D298A-F: 5' TATCCGTCCGGCGTCTGGTGACCC 3' (SEQ ID NO: 14) and D298A-R: 5' GGGTCACCAGACGCCGGACGGATA 3' (SEQ ID NO: 15) were used. The plasmid pRSET-31 constructed in Subsection 17 in Section II of Example 6 was used as a template. The E231Q/D298A/D338E/D377E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Section I of Example 6 for details) to obtain plasmid pRSET-41. The plasmid pRSET-41 was transformed into competent bacterial cells E. coli BL21, and clones having Nampt activity were screened out on a Luria broth (LB) plate (containing 50 mg/L Kanamycin). Plasmid pRSET-41 DNA was extracted from the clone, and sequenced to determine that the point mutation introduced was correct. Compared with the parent amino acid sequence as shown in SEQ ID NO: 2, the amino acid sequence of the E231Q/D298A/D338E/D377E mutant has a mutation of Glu (E) to Gln (Q) at position 231, a mutation of Asp (D) to Ala (A) at position 298, a mutation of Asp (D) to Glu (E) at position 338, and a mutation of Asp (D) to Glu (E) at position 377.

III. Extraction of Enzymes

The plasmid pRSET-nampt containing parent Nampt gene, and the plasmid pRSET-F180A, pRSET-F180W, pRSET-A182Y, pRSET-E231A, pRSET-E231Q, pRSET-D298A, pRSET-D298N, pRSET-D298E, pRSET-D338N, pRSET-D338E, pRSET-D377A, pRSET-D377N, pRSET-D377E, pRSET-21, pRSET-22, pRSET-23, pRSET-31, and pRSET-41 containing Nampt mutant genes were respectively transformed into competent bacterial cells E. coli BL21, and incubated for 24 hrs on a Luria broth (LB) plate (containing 50 mg/L Kanamycin) at 37° C. Individual clones were inoculated in 50 ml of LB liquid medium (containing 50 mg/L Kanamycin), and incubated for 16-20 hrs at 30° C. The bacterial cells were collected by centrifugation, and the same amount of cells were weighed and suspended in a cell lysis buffer (pH 7.5) at a ratio of 1:4. The bacterial cells were ultrasonically lyzed. After centrifugation (4-10° C., 12000 rpm, 10 min), the supernatant was collected, that is, the protein supernatant of parent Nampt and a series of Nampt mutants was obtained respectively, which could be used in the enzyme activity assay and in the preparation of NMN by biocatalysis.

IV. Enzyme Activity Assay

A substrate solution containing 60 mM nicotinamide, 25 mM PRPP, 18 mM $MgCl_2$, 15 mM KCl, and 100 mM Tris buffer was formulated and adjusted to pH 7.5. 19 portions of the substrate solution (each 900 μl) were taken, then added respectively to 100 μl of equal concentration of the protein supernatant of parent Nampt and a series of Nampt mutants obtained in Section III of Example 6, and reacted for 10 min at 37° C. The reaction was terminated by adding 100 μL of 25% trichloroacetic acid. The NMN content in the reaction solution was determined by HPLC, and the specific activity of each enzyme was calculated.

Where the specific activity of parent Nampt was assumed to be 100, the relative specific activity of the parent and the mutants are as shown in Table 1.

TABLE 1

| Enzyme activity of Nampt | |
|---|---|
| Name of enzyme | Relative specific activity |
| Parent | 100 |
| F180A mutant | 118 |
| F180W mutant | 122 |
| A182Y mutant | 187 |
| E231A mutant | 221 |
| E231Q mutant | 529 |
| D298A mutant | 236 |
| D298N mutant | 238 |
| D298E mutant | 149 |
| D338N mutant | 194 |
| D338E mutant | 516 |
| D377A mutant | 204 |
| D377N mutant | 279 |
| D377E mutant | 274 |
| E231Q/D338E mutant | 593 |
| E231Q/D377E mutant | 546 |
| D338E/D377E mutant | 601 |
| E231Q/D338E/D377E mutant | 654 |
| E231Q/D298A/D338E/D377E mutant | 691 |

V. Preparation of NMN

A substrate solution containing 30 mM nicotinamide, 20 mMATP, 30 mM ribose, 15 mM $MgCl_2$, 15 mM KCl, and 100 mM Tris-HCl buffer was added to a reactor, and adjusted to pH7.0-7.5. Then, various catalytic enzymes were added to the substrate solution in amounts of: 10 ml of the protein supernatant of Nampt mutant (F180A) prepared in Section III of Example 6/L of substrate solution, 20 g of ribose phosphate pyrophosphokinase/L of substrate solution, 20 g of ribokinase/L of substrate solution. The system was stirred until uniform and then reacted. During the reaction process, stirring was continued (at a stirring speed of 50 rpm), the reaction temperature was controlled at 37° C., and the pH was maintained at 7.0-7.5. After 4 hrs of reaction, a crude NMN product solution (containing 10 mM NMN) was obtained, which was filtered, purified, and dried, to obtain a product NMN.

What is claimed is:

1. A method for preparing nicotinamide mononucleotide (NMN), comprising: catalytically reacting a plurality of raw materials comprising nicotinamide, ATP, and ribose in the presence of nicotinamide phosphoribosyltransferase (Nampt), ribose phosphate pyrophosphokinase, and ribokinase, to prepare the NMN,
wherein the Nampt is a protein derived from a protein having the amino acid sequence of SEQ ID NO: 2, wherein the amino acid sequence of the Nampt differs from the amino acid sequence of SEQ ID NO: 2 in that the Nampt has a mutation; wherein the mutation is selected from the group consisting of F180A, F180W, A182Y, E231A, E231Q, D298A, D298N, D298E, D338N, D338E, D377A, D377N, D377E, a combination of E231Q and D338E, a combination of E231Q and D377E, a combination of D338E and D377E, a combination of E231Q, D338E and D377E, and a combination of E231Q, D298A, D338E and D377E.

2. The method for preparing NMN according to claim 1, wherein the reaction takes place at a temperature of 30-50° C. and a pH of 6.5-8.5.

3. The method for preparing NMN according to claim 1, wherein the reaction takes place in the presence of $Mg^{2+}$ and $K^+$.

4. The method for preparing NMN according to claim 1, wherein the reaction takes place in Tris-HCl buffer.

5. The method for preparing NMN according to claim 1, wherein a concentration of the nicotinamide is 1-150 mM, a concentration of the ATP is 1-50 mM, and a concentration of the ribose is 1-100 mM.

6. The method for preparing NMN according to claim 1, wherein a molar ratio of the raw materials of nicotinamide, ATP, to ribose is 1-4:1:1-4.

7. The method for preparing NMN according to claim 6, wherein the molar ratio of the raw materials of nicotinamide, ATP, to ribose is 1.5:1:1.5.

* * * * *

SEQUENCE LISTING

<160> NUMBER OF SEQ ID NOS: 29

<210> SEQ ID NO 1
<211> LENGTH: 1392
<212> TYPE: DNA
<213> ORGANISM: Unknown
<220> FEATURE:
<223> OTHER INFORMATION: Meiothermus ruber DSM 1279

<400> SEQUENCE: 1

```
atgaaaaccc tcaaccccca caacctcatc ctcaacaccg acagctacaa agccagtcac      60
tttgcccagt tccccaaagg catgacctat gccagttggt acatcgagag ccggggcggc     120
gactcgaatt ttgtgcgttt ctttggccta caggccttct taatcgagta cctcagcaaa     180
ggggtcagcc tggccgatgt ggaggaggcc caggaagttt tcctggccca cggcctgccc     240
ttccccacag aaggctggcg ctacatcgct caggacttag agggcggct gccggtgcgc      300
atccgggccg tgcccgaggg taaggtggtt cccgtacaca ccccctggt catcatcgag       360
agcaccgacc ccaaagtgcc ctggctgccg ggttggctcg agaccgcgct gctgcgggcg     420
gtctggtacc ccaccacggt ctgcacggtc tcctggggta ccgcaacac catcaaggag      480
tacctggaga aaccgccga cgaccccgag gccgagctgc ccttcaagct gcacgacttt      540
ggcgcgcgcg gggtgagcag cctcgagagc gccgggctgg gcgggatggc ccacctggtg     600
aactttatgg gcaccgacac cgtcaccgcc ctgatctacg cccgcaacta ctacggggcc     660
gagatggccg gctacagcat cccggccatg gagcacagca ccgtgaccag ctttggccgc     720
accggcgagg cccaggccta ccgccagatg ctcgagacct ttgccaagcc ggggccctg      780
atggccatgt gattgattc gtacaaccgc gagcacgccg tgggccagat tatccggcgaa    840
gaactgcgcg agctcatcca gcagtcgggg gccaccgtgg tcatccggcc gactcgggc     900
gacccgccct tcgtggtgct gcgcaccgtg cagaccctcg aggccaaatt tggcgccacc     960
ctcaaccgca agggctacaa ggtgctgaac ggggtgcggg tcatccaggg cgatggggtg    1020
aacgccgact ccatccgcaa ggtgctgttt ttgctcgagc agtggggcta cagcgcctcc    1080
aacgtggcct tcggcatggg cggggccctc ttgcagcacc cccaccgcga tacccagaag    1140
ttcgcccaga agctgcacct ggtcacggtg aacggcgaga cctacggggt gggcaagagc    1200
ccggtggacg accccggcaa actctccaag aagggccgtc tggacgttat ccaggacgag    1260
cgcggcatcc gcacggtgga gctgccgctg gaggccgccc agccgcaccc ccagagcatc    1320
ctgcaaaccg tattcgagaa cgggtcgatt acccggcgct acacctggga agaggtgcgc    1380
aacaacgctt ag                                                        1392
```

<210> SEQ ID NO 2
<211> LENGTH: 463
<212> TYPE: PRT
<213> ORGANISM: Unknown
<220> FEATURE:
<223> OTHER INFORMATION: Meiothermus ruber DSM 1279

<400> SEQUENCE: 2

```
Met Lys Thr Leu Asn Pro His Asn Leu Ile Leu Asn Thr Asp Ser Tyr
1               5                   10                  15

Lys Ala Ser His Phe Ala Gln Phe Pro Lys Gly Met Thr Tyr Ala Ser
                20                  25                  30

Trp Tyr Ile Glu Ser Arg Gly Gly Asp Ser Asn Phe Val Arg Phe Phe
            35                  40                  45
```

```
Gly Leu Gln Ala Phe Leu Ile Glu Tyr Leu Ser Lys Gly Val Ser Leu
 50                  55                  60

Ala Asp Val Glu Glu Ala Gln Glu Val Phe Leu Ala His Gly Leu Pro
 65                  70                  75                  80

Phe Pro Thr Glu Gly Trp Arg Tyr Ile Ala Gln Asp Leu Gly Gly Arg
                 85                  90                  95

Leu Pro Val Arg Ile Arg Ala Val Pro Glu Gly Lys Val Val Pro Val
                100                 105                 110

His Asn Pro Leu Val Ile Ile Glu Ser Thr Asp Pro Lys Val Pro Trp
            115                 120                 125

Leu Pro Gly Trp Leu Glu Thr Ala Leu Leu Arg Ala Val Trp Tyr Pro
130                 135                 140

Thr Thr Val Cys Thr Val Ser Trp Gly Ile Arg Asn Thr Ile Lys Glu
145                 150                 155                 160

Tyr Leu Glu Lys Thr Ala Asp Asp Pro Glu Ala Glu Leu Pro Phe Lys
                165                 170                 175

Leu His Asp Phe Gly Ala Arg Gly Val Ser Ser Leu Glu Ser Ala Gly
            180                 185                 190

Leu Gly Gly Met Ala His Leu Val Asn Phe Met Gly Thr Asp Thr Val
        195                 200                 205

Thr Ala Leu Ile Tyr Ala Arg Asn Tyr Tyr Gly Ala Glu Met Ala Gly
210                 215                 220

Tyr Ser Ile Pro Ala Met Glu His Ser Thr Val Thr Ser Phe Gly Arg
225                 230                 235                 240

Thr Gly Glu Ala Gln Ala Tyr Arg Gln Met Leu Glu Thr Phe Ala Lys
                245                 250                 255

Pro Gly Ala Leu Met Ala Met Val Ile Asp Ser Tyr Asn Arg Glu His
            260                 265                 270

Ala Val Gly Gln Ile Ile Gly Glu Glu Leu Arg Glu Leu Ile Gln Gln
        275                 280                 285

Ser Gly Ala Thr Val Val Ile Arg Pro Asp Ser Gly Asp Pro Pro Phe
290                 295                 300

Val Val Leu Arg Thr Val Gln Thr Leu Glu Ala Lys Phe Gly Ala Thr
305                 310                 315                 320

Leu Asn Arg Lys Gly Tyr Lys Val Leu Asn Gly Val Arg Val Ile Gln
                325                 330                 335

Gly Asp Gly Val Asn Ala Asp Ser Ile Arg Lys Val Leu Phe Leu Leu
            340                 345                 350

Glu Gln Trp Gly Tyr Ser Ala Ser Asn Val Ala Phe Gly Met Gly Gly
        355                 360                 365

Ala Leu Leu Gln His Pro His Arg Asp Thr Gln Lys Phe Ala Gln Lys
370                 375                 380

Leu His Leu Val Thr Val Asn Gly Glu Thr Tyr Gly Val Gly Lys Ser
385                 390                 395                 400

Pro Val Asp Asp Pro Gly Lys Leu Ser Lys Lys Gly Arg Leu Asp Val
                405                 410                 415

Ile Gln Asp Glu Arg Gly Ile Arg Thr Val Glu Leu Pro Leu Glu Ala
            420                 425                 430

Ala Gln Pro His Pro Gln Ser Ile Leu Gln Thr Val Phe Glu Asn Gly
        435                 440                 445

Ser Ile Thr Arg Arg Tyr Thr Trp Glu Glu Val Arg Asn Asn Ala
450                 455                 460
```

-continued

```
<210> SEQ ID NO 3
<211> LENGTH: 463
<212> TYPE: PRT
<213> ORGANISM: Artificial Sequence
<220> FEATURE:
<223> OTHER INFORMATION: F180A mutant

<400> SEQUENCE: 3

Met Lys Thr Leu Asn Pro His Asn Leu Ile Leu Asn Thr Asp Ser Tyr
1               5                   10                  15

Lys Ala Ser His Phe Ala Gln Phe Pro Lys Gly Met Thr Tyr Ala Ser
                20                  25                  30

Trp Tyr Ile Glu Ser Arg Gly Gly Asp Ser Asn Phe Val Arg Phe Phe
            35                  40                  45

Gly Leu Gln Ala Phe Leu Ile Glu Tyr Leu Ser Lys Gly Val Ser Leu
        50                  55                  60

Ala Asp Val Glu Glu Ala Gln Glu Val Phe Leu Ala His Gly Leu Pro
65                  70                  75                  80

Phe Pro Thr Glu Gly Trp Arg Tyr Ile Ala Gln Asp Leu Gly Gly Arg
                85                  90                  95

Leu Pro Val Arg Ile Arg Ala Val Pro Glu Gly Lys Val Val Pro Val
            100                 105                 110

His Asn Pro Leu Val Ile Ile Glu Ser Thr Asp Pro Lys Val Pro Trp
        115                 120                 125

Leu Pro Gly Trp Leu Glu Thr Ala Leu Leu Arg Ala Val Trp Tyr Pro
130                 135                 140

Thr Thr Val Cys Thr Val Ser Trp Gly Ile Arg Asn Thr Ile Lys Glu
145                 150                 155                 160

Tyr Leu Glu Lys Thr Ala Asp Asp Pro Glu Ala Glu Leu Pro Phe Lys
                165                 170                 175

Leu His Asp Ala Gly Ala Arg Gly Val Ser Ser Leu Glu Ser Ala Gly
            180                 185                 190

Leu Gly Gly Met Ala His Leu Val Asn Phe Met Gly Thr Asp Thr Val
        195                 200                 205

Thr Ala Leu Ile Tyr Ala Arg Asn Tyr Tyr Gly Ala Glu Met Ala Gly
210                 215                 220

Tyr Ser Ile Pro Ala Met Glu His Ser Thr Val Thr Ser Phe Gly Arg
225                 230                 235                 240

Thr Gly Glu Ala Gln Ala Tyr Arg Gln Met Leu Glu Thr Phe Ala Lys
                245                 250                 255

Pro Gly Ala Leu Met Ala Met Val Ile Asp Ser Tyr Asn Arg Glu His
            260                 265                 270

Ala Val Gly Gln Ile Ile Gly Glu Glu Leu Arg Glu Leu Ile Gln Gln
        275                 280                 285

Ser Gly Ala Thr Val Val Ile Arg Pro Asp Ser Gly Asp Pro Pro Phe
290                 295                 300

Val Val Leu Arg Thr Val Gln Thr Leu Glu Ala Lys Phe Gly Ala Thr
305                 310                 315                 320

Leu Asn Arg Lys Gly Tyr Lys Val Leu Asn Gly Val Arg Val Ile Gln
                325                 330                 335

Gly Asp Gly Val Asn Ala Asp Ser Ile Arg Lys Val Leu Phe Leu Leu
            340                 345                 350

Glu Gln Trp Gly Tyr Ser Ala Ser Asn Val Ala Phe Gly Met Gly Gly
        355                 360                 365

Ala Leu Leu Gln His Pro His Arg Asp Thr Gln Lys Phe Ala Gln Lys
```

-continued

```
             370                 375                 380
Leu His Leu Val Thr Val Asn Gly Glu Thr Tyr Gly Val Gly Lys Ser
385                 390                 395                 400

Pro Val Asp Asp Pro Gly Lys Leu Ser Lys Lys Gly Arg Leu Asp Val
                405                 410                 415

Ile Gln Asp Glu Arg Gly Ile Arg Thr Val Glu Leu Pro Leu Glu Ala
                420                 425                 430

Ala Gln Pro His Pro Gln Ser Ile Leu Gln Thr Val Phe Glu Asn Gly
                435                 440                 445

Ser Ile Thr Arg Arg Tyr Thr Trp Glu Glu Val Arg Asn Asn Ala
    450                 455                 460

<210> SEQ ID NO 4
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 4
gttcaaactg cacgacgcgg gtgctcgtgg tgtttc                            36

<210> SEQ ID NO 5
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 5
gaaacaccac gagcacccgc gtcgtgcagt ttgaac                            36

<210> SEQ ID NO 6
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 6
gttcaaactg cacgactggg gtgctcgtgg tgtttc                            36

<210> SEQ ID NO 7
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 7
gaaacaccac gagcaccccA gtcgtgcagt ttgaac                            36

<210> SEQ ID NO 8
<211> LENGTH: 40
<212> TYPE: DNA
<213> ORGANISM: Artificial Sequence
<220> FEATURE:
<223> OTHER INFORMATION: the sequence is synthetized

<400> SEQUENCE: 8
caaactgcac gacttcggtt atcgtggtgt ttcttctctg                        40

<210> SEQ ID NO 9
```

```
<211> LENGTH: 40
<212> TYPE: DNA
<213> ORGANISM: Artificial Sequence
<220> FEATURE:
<223> OTHER INFORMATION: the sequence is synthetized

<400> SEQUENCE: 9
cagagaagaa acaccacgat aaccgaagtc gtgcagtttg                                40

<210> SEQ ID NO 10
<211> LENGTH: 31
<212> TYPE: DNA
<213> ORGANISM: Artificial Sequence
<220> FEATURE:
<223> OTHER INFORMATION: the sequence is synthetized

<400> SEQUENCE: 10
ctatcccggc tatggcgcac tctaccgtta c                                         31

<210> SEQ ID NO 11
<211> LENGTH: 31
<212> TYPE: DNA
<213> ORGANISM: Artificial Sequence
<220> FEATURE:
<223> OTHER INFORMATION: the sequence is synthetized

<400> SEQUENCE: 11
gtaacggtag agtgcgccat agccgggata g                                         31

<210> SEQ ID NO 12
<211> LENGTH: 34
<212> TYPE: DNA
<213> ORGANISM: Artificial Sequence
<220> FEATURE:
<223> OTHER INFORMATION: the sequence is synthetized

<400> SEQUENCE: 12
ctctatcccg gctatgcagc actctaccgt tacc                                      34

<210> SEQ ID NO 13
<211> LENGTH: 34
<212> TYPE: DNA
<213> ORGANISM: Artificial Sequence
<220> FEATURE:
<223> OTHER INFORMATION: the sequence is synthetized

<400> SEQUENCE: 13
ggtaacggta gagtgctgca tagccgggat agag                                      34

<210> SEQ ID NO 14
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 14
tatccgtccg gcgtctggtg accc                                                 24

<210> SEQ ID NO 15
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 15
```
gggtcaccag acgccggacg gata                                          24

<210> SEQ ID NO 16
<211> LENGTH: 33
<212> TYPE: DNA
<213> ORGANISM: Artificial Sequence
<220> FEATURE:
<223> OTHER INFORMATION: the sequence is synthetized

<400> SEQUENCE: 16
gttgttatcc gtccgaattc tggtgacccg ccg                                33

<210> SEQ ID NO 17
<211> LENGTH: 33
<212> TYPE: DNA
<213> ORGANISM: Artificial Sequence
<220> FEATURE:
<223> OTHER INFORMATION: the sequence is synthetized

<400> SEQUENCE: 17
cggcgggtca ccagaattcg gacggataac aac                                33

<210> SEQ ID NO 18
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 18
gttgttatcc gtccggaatc tggtgacccg ccgttc                             36

<210> SEQ ID NO 19
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 19
gaacggcggg tcaccagatt ccggacggat aacaac                             36

<210> SEQ ID NO 20
<211> LENGTH: 38
<212> TYPE: DNA
<213> ORGANISM: Artificial Sequence
<220> FEATURE:
<223> OTHER INFORMATION: the sequence is synthetized

<400> SEQUENCE: 20
gttcgtgtta tccagggtaa tggtgttaac gctgactc                           38

<210> SEQ ID NO 21
<211> LENGTH: 38
<212> TYPE: DNA
<213> ORGANISM: Artificial Sequence
<220> FEATURE:
<223> OTHER INFORMATION: the sequence is synthetized

<400> SEQUENCE: 21
gagtcagcgt taacaccatt accctggata acacgaac                           38

<210> SEQ ID NO 22
<211> LENGTH: 30
<212> TYPE: DNA

```
<213> ORGANISM: Artificial Sequence
<220> FEATURE:
<223> OTHER INFORMATION: the sequence is synthetized

<400> SEQUENCE: 22
gttatccagg gtgaaggtgt taacgctgac                                      30

<210> SEQ ID NO 23
<211> LENGTH: 30
<212> TYPE: DNA
<213> ORGANISM: Artificial Sequence
<220> FEATURE:
<223> OTHER INFORMATION: the sequence is synthetized

<400> SEQUENCE: 23
gtcagcgtta acaccttcac cctggataac                                      30

<210> SEQ ID NO 24
<211> LENGTH: 27
<212> TYPE: DNA
<213> ORGANISM: Artificial Sequence
<220> FEATURE:
<223> OTHER INFORMATION: the sequence is synthetized

<400> SEQUENCE: 24
cacccgcacc gtgcgaccca gaaattc                                         27

<210> SEQ ID NO 25
<211> LENGTH: 27
<212> TYPE: DNA
<213> ORGANISM: Artificial Sequence
<220> FEATURE:
<223> OTHER INFORMATION: the sequence is synthetized

<400> SEQUENCE: 25
gaatttctgg gtcgcacggt gcgggtg                                         27

<210> SEQ ID NO 26
<211> LENGTH: 35
<212> TYPE: DNA
<213> ORGANISM: Artificial Sequence
<220> FEATURE:
<223> OTHER INFORMATION: the sequence is synthetized

<400> SEQUENCE: 26
gcaacacccg caccgtaata cccagaaatt cgctc                                35

<210> SEQ ID NO 27
<211> LENGTH: 35
<212> TYPE: DNA
<213> ORGANISM: Artificial Sequence
<220> FEATURE:
<223> OTHER INFORMATION: the sequence is synthetized

<400> SEQUENCE: 27
gagcgaattt ctgggtatta cggtgcgggt gttgc                                35

<210> SEQ ID NO 28
<211> LENGTH: 26
<212> TYPE: DNA
<213> ORGANISM: Artificial Sequence
<220> FEATURE:
<223> OTHER INFORMATION: the sequence is synthetized

<400> SEQUENCE: 28
cccgcaccgt gaaacccaga aattcg                                          26
```

```
<210> SEQ ID NO 29
<211> LENGTH: 26
<212> TYPE: DNA
<213> ORGANISM: Artificial Sequence
<220> FEATURE:
<223> OTHER INFORMATION: the sequence is synthetized

<400> SEQUENCE: 29
cgaatttctg ggtttcacgg tgcggg                                          26
```